United States Patent [19]
Christensen

[11] Patent Number: 5,651,942
[45] Date of Patent: Jul. 29, 1997

[54] AROMATIC FRAGRANCE GENERATOR

[76] Inventor: Arthur E. Christensen, 1316 Dulaney Valley Rd., Towson, Md. 21286

[21] Appl. No.: 584,740

[22] Filed: Jan. 11, 1996

[51] Int. Cl.⁶ .................................................. A61L 9/03
[52] U.S. Cl. ........................ 422/125; 422/5; 422/305
[58] Field of Search .................... 422/5, 120, 122, 422/123, 125, 305

[56] References Cited

U.S. PATENT DOCUMENTS

| | | | |
|---|---|---|---|
| 2,469,656 | 5/1949 | Lienert | 219/45 |
| 2,668,993 | 2/1954 | Bair | 422/125 |
| 3,948,445 | 4/1976 | Andeweg | 239/53 |
| 3,959,642 | 5/1976 | Turro | 422/125 X |
| 4,005,334 | 1/1977 | Andrews | 315/208 |
| 4,009,384 | 2/1977 | Holland | 240/108 R |
| 4,146,566 | 3/1979 | Gaiser | 422/123 X |
| 4,214,146 | 7/1980 | Schimanski | 219/274 |
| 4,346,059 | 8/1982 | Spector | 422/125 |
| 4,425,302 | 1/1984 | Pons Pons | 422/125 |
| 4,695,434 | 9/1987 | Spector | 422/116 |
| 4,781,895 | 11/1988 | Spector | 422/125 |
| 5,032,360 | 7/1991 | Houston | 422/4 |
| 5,069,877 | 12/1991 | Pozzo | 422/4 |
| 5,269,723 | 12/1993 | Bender | 422/124 X |

*Primary Examiner*—Robert J. Warden
*Assistant Examiner*—E. Leigh Dawson
*Attorney, Agent, or Firm*—Leonard Bloom

[57] ABSTRACT

A device for supplying aromatic fragrances to the atmosphere employs a heating element in a container to heat a fragrance base material contained in a receptacle to supply a pleasant aroma to the atmosphere, primarily to eliminate bathroom and kitchen odors.

14 Claims, 9 Drawing Sheets

AROMATIC FRAGRANCE GENERATOR

CROSS REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX SPECIFYING THE TOTAL NUMBER OF MICROFICHE AND TOTAL NUMBER OF FRAMES

Not applicable

BACKGROUND OF THE INVENTION

Different methods for supplying fragrances and deodorizing the atmosphere are well known in the art. However, there exists a need for supplying fragrances and deodorizers in a manner which is simple, convenient and inexpensive. Further, there is a need to supply a simple apparatus which can be used along with simple household herbs and spices, and where as the occasion or desire arises a different type of fragrance, aroma or deodorant can be supplied and used in the apparatus. A preferred method would use fragrances and spices conveniently found in the home to supply the aroma.

Prior Art Patents

Lienert in U.S. Pat. No. 2,469,656 discloses a vaporizer having an electric light bulb to generate a source of heat to vaporize a liquid held on a wick.

A vapor generator with an electric heater for vaporizing an air freshening material is described by Andeweg in U.S. Pat. No. 3,948,445. This vapor generator can vaporize material in the form of granules or pellets.

U.S. Pat. No. 4,009,384 to Holland discloses an electric lamp to produce a pleasing scent. The Holland device embodies a sheet of porous fabric which has absorbed therein bath oil, perfume or cologne. The porous fabric is fashioned into an article to fit into the post of a lamp holding a lamp shade.

Schimanski in U.S. Pat. No. 4,214,146 teaches an electrically heated vaporizer. The vaporizer employs an impregnated member which can be replaced once the volatile material is exhausted.

U.S. Pat. No. 4,346,059 to Spector discloses an aroma-generating lamp employing a light bulb to vaporize a liquid which has been sprayed onto an absorbent pad in proximity with the bulb.

Pons in U.S. Pat. No. 4,425,302 teaches a household electric device which sublimes perfumed bars. The bar is housed in a compartment and receives heat necessary for slow sublimation of perfume from the compartment.

An aroma-generating unit adapted to periodically discharge an aromatic vapor into the atmosphere is taught by Spector in U.S. Pat. No. 4,695,434. The Spector device has a replaceable cartridge containing a porous mat impregnated with an aromatic liquid. The aromatic liquid is intermittently discharged into the air by heating air confined in a chamber. In this way a positive pressure is created which forces the heated air through a port, as well as through an impregnated mat to rapidly volatilize the aromatic liquid.

Houston in U.S. Pat. No. 5,032,360 discloses an odor remover using a candle which causes heated room air to be absorbed by charcoal and thereby purifying the air.

A device for diffusing active volatile substances such as perfume into the air is disclosed in U.S. Pat. No. 5,069,877 to Pozzo. The diffusing device comprises a support element having absorbed therein a volatile substance packaged in a heat shrink material. The volatile substance is released when temperature, as well as the pressure are exerted to heat shrink the material.

BRIEF SUMMARY OF THE INVENTION

An object of this invention is to provide a simple and inexpensive device for producing a pleasant aromatic atmosphere.

Another object is to produce a device in which common household ingredients can be used to produce a pleasant aroma or fragrance for deodorization.

An important object of this invention is its ability to use granular material as the aroma producing agent.

A major object of this invention is to make an aroma generator out of easy to obtain materials.

The present invention relates to an aroma generator for producing a fragrant aroma into the ambient atmosphere, in a convenient and inexpensive manner. The aroma-generating device requires no complicated apparatus to vaporize the fragrance; nor are expensive fragrances or fragrance bases required. Costly proprietary products do not have to be used in the aroma generating apparatus of this invention because the aromatic fragrance generator can employ simple household items as the aromatic base, instead of expensive proprietary deodorizers. The ordinary consumer will find the aromatic fragrance device of this invention to be of great economic advantage.

The herein described invention in a broad aspect involves a device for supplying a pleasant aroma or fragrance to the atmosphere. The device comprises in combination an external container having a closed bottom, an open top and side walls. The side walls have a plurality of spaced-apart air-vent holes located near the bottom of the container. The external container contains therein at its bottom a heating element and surrounding and extending over said heating element there is provided a ventilated support. The support provides a base for retaining a fragrance base receptacle or a fragrance base heating pan, as well as providing for air from the air-vent holes to pass through the passage at the bottom of the support, thereby creating a draft. Above said fragrance base receptacle and sealing the open top of the external container is a vented cover. When an aromatic fragrance base is placed in said fragrance receptacle and the heating element turned on, the fragrance base will be heated to produce a fragrant aroma to the ambient atmosphere by convection.

The external container may be cylindrical and have a heating element attached at its bottom. The fragrance base receptacle or heating pan can be supplied with a handle to facilitate its removal from the support and external container.

In a preferred embodiment the fragrance generator has parts in which the external container, ventilated support and fragrance base receptacle are all cylindrical; however, other configurations such as square or hexagonal would be operative. The external container, ventilated support and heating pan are made of metal in the preferred embodiment; however, it is conceptually possible to make them of other materials such as plastic.

Among the fragrance bases which can be used to produce a pleasant aroma are cinnamon, nutmeg, ginger, clove, mint, peppermint, and coffee. Various food spices could be used to produce a pleasant aroma and stimulate the appetite. In addition perfumes and various bouquets of the same could be used. Varied combinations of spices and perfumes could be employed to produce unique olfactory sensations.

Viewed in yet another aspect, the present invention provides a fragrance generator intended for household purposes. The generator includes housing having an electrical socket therein, and a replaceable low-wattage inexpensive-to-operate light bulb screwed into the socket. Means are provided, including a switch, for selectively energizing the bulb, thereby providing a source of heat within the housing. A pan is disposed within the housing, in juxtaposition to the bulb, and contains a granular material heated by the bulb. Means are also provided in the housing for the inlet of air into the housing, for circulation therein and through or around the pan of heated granular material, and discharge out of the housing, thereby creating a pleasant aroma.

As an alternative embodiment, the device for supplying a pleasant aroma to the atmosphere comprises an external container having a closed bottom, an open top and side walls, with said side walls having toward their bottom air-vent holes. The external container contains therein at its bottom a heating element. Extending over said heating element there is provided a fragrance base receptacle supported by legs. In a preferred embodiment three legs are provided. Above said fragrance base receptacle and sealing the open top of said external container is a vented cover.

As a further alternative embodiment the aromatic fragrance generator the external container is provided with air-vent holes in the bottom of the external container, instead of at the bottom of the side walls of the container. In addition the bottom of the external container is provided with legs. These legs raise the container above its seating surface and allow for the access of air into the air-vent holes in the bottom of the external container.

Viewed another way the generator is made of an external container provided with a bottom having air-vent holes. Legs are provided at the bottom of the external container upon which the generator can stand and allow access of air into the air-vent holes. Within the container at its bottom is a heating element. Surrounding and extending over said heating element is a ventilated support. Said ventilated support provides a base for retaining a fragrance base receptacle, as well as providing for air from the air-vent holes to pass through to and create a draft. Above said fragrance base receptacle and sealing the open top of said external container is a vented cover, such that when an aromatic fragrance base is placed in said fragrance base receptacle and the heating element turned on, the fragrance base will aromatize and produce a pleasant aroma to the ambient atmosphere. The device may have three or more legs and may have a single or multiple air-vent holes therein. It is obvious that the generator with legs on the external container can be used with the fragrance base receptacle supported by legs.

The objects set forth above, as well as other objects of the present invention will become apparent from a reading of the following specification taken in conjunction with the enclosed drawings.

DESCRIPTION

Figure 1:
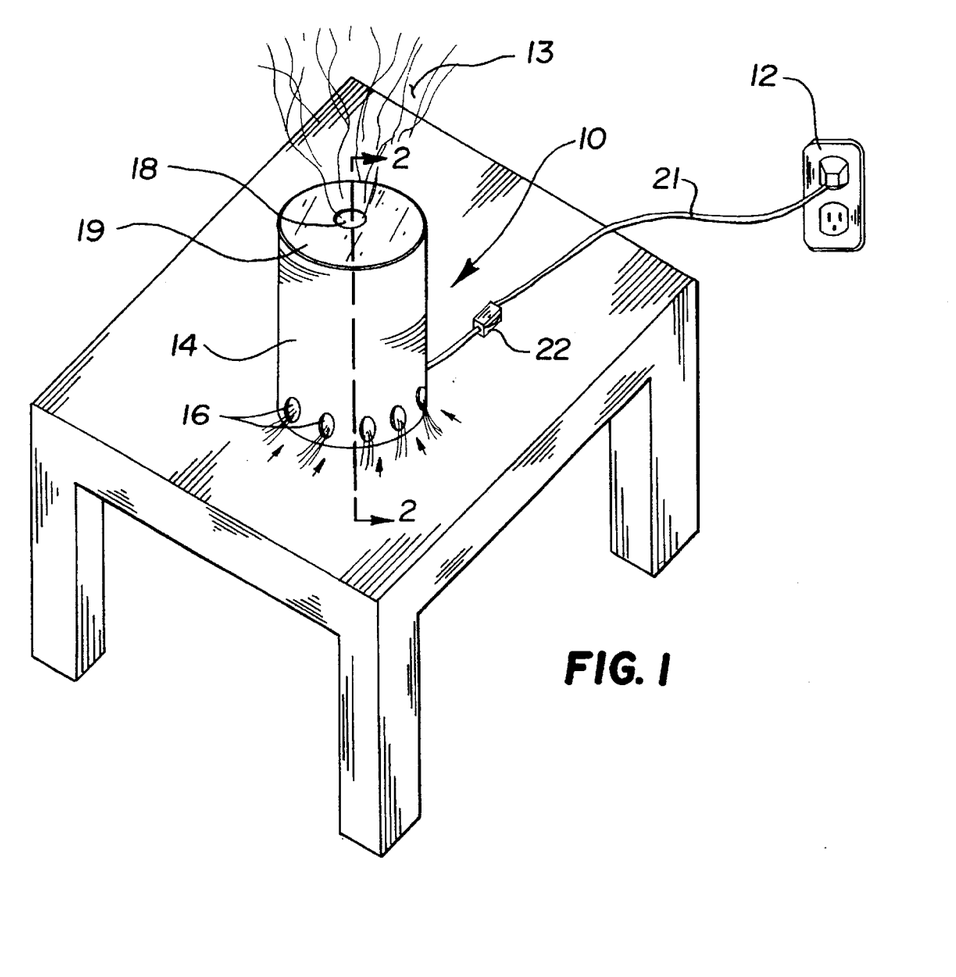
FIG. 1 is a perspective view illustrating the aromatic fragrance generator of this invention.
Figure 2:
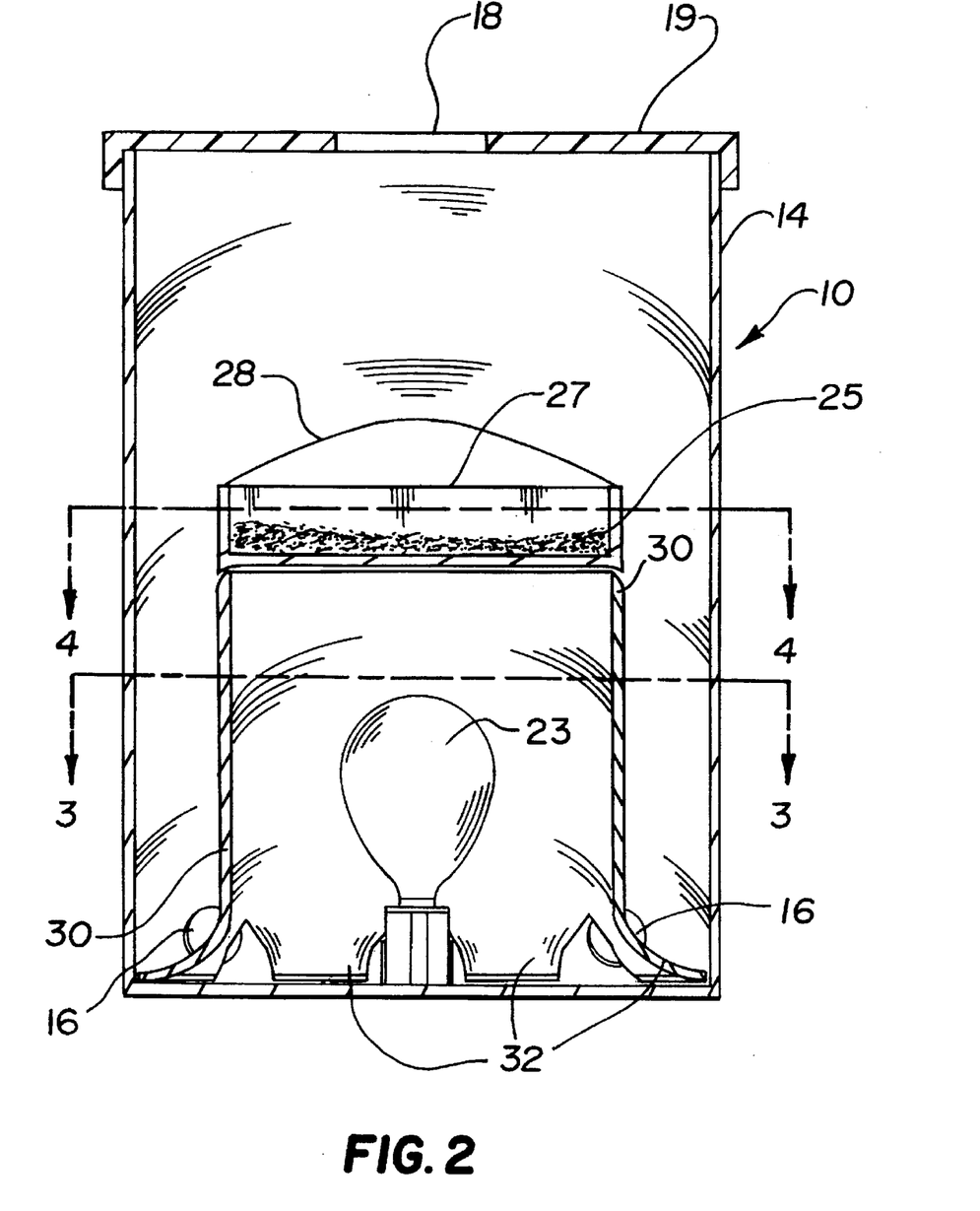
FIG. 2 is a sectional view taken along lines 2—2 of FIG. 1.
Figure 3:
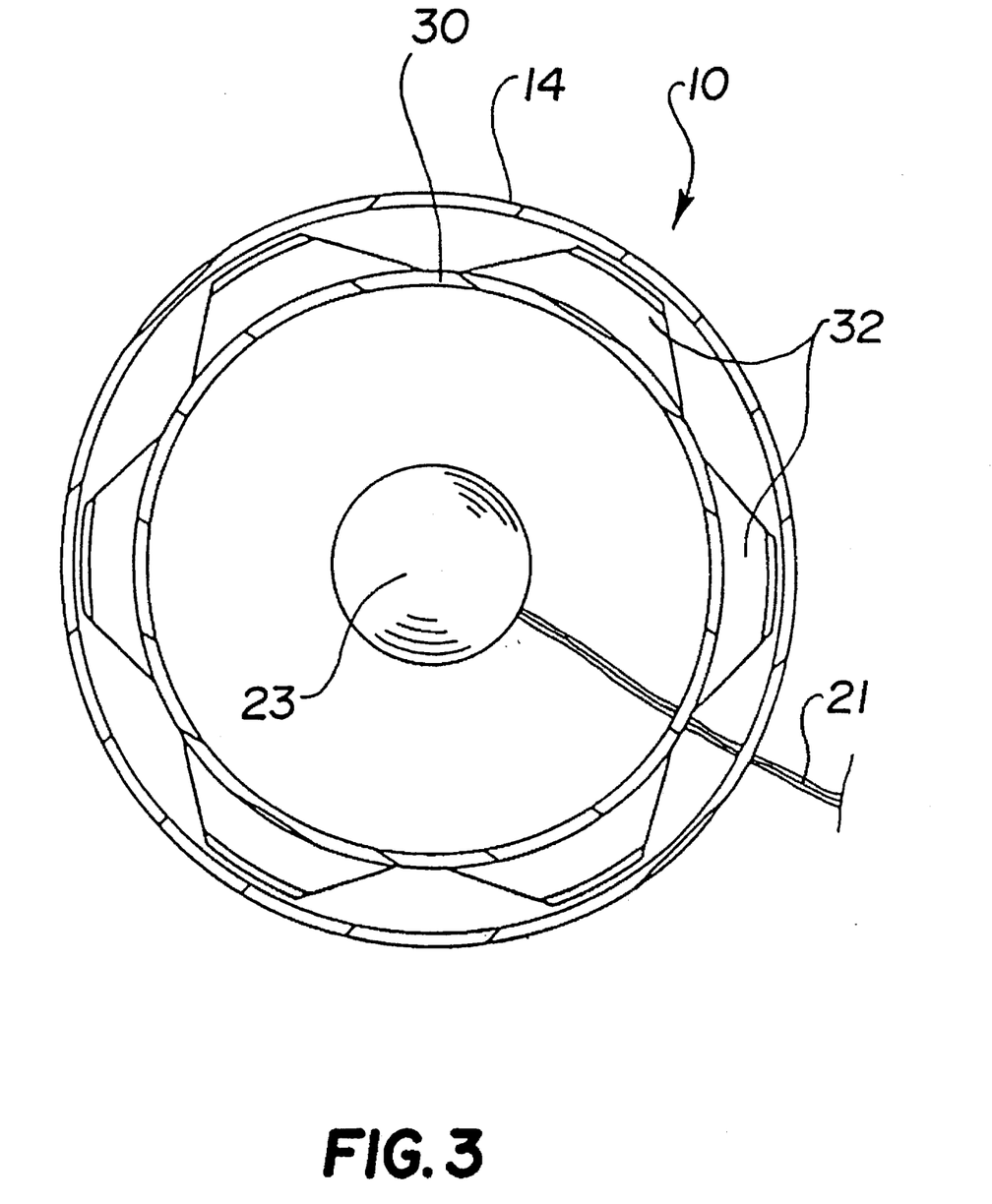
FIG. 3 is a sectional view taken along lines 3—3 of FIG. 2.
Figure 4:
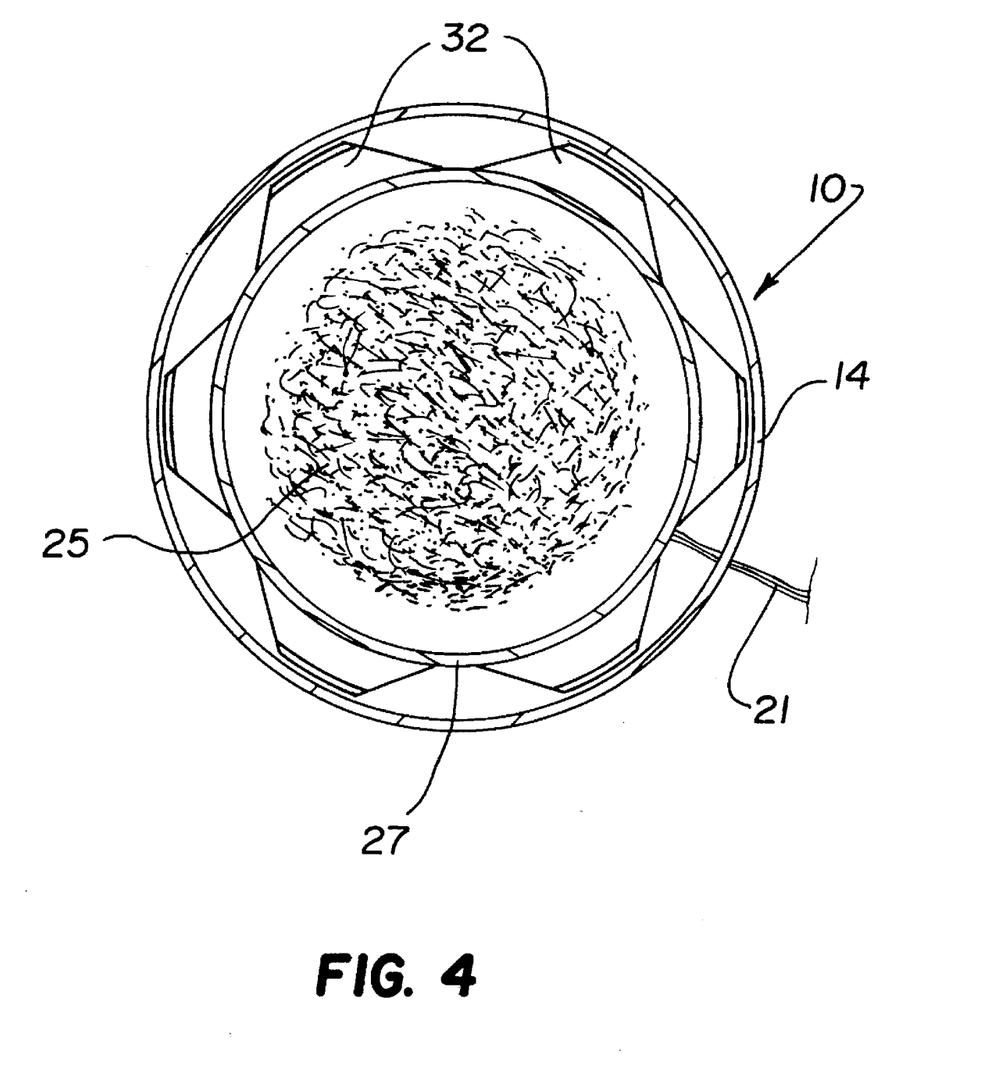
FIG. 4 is a sectional view taken along lines 4—4 of FIG. 2.

With reference to FIG. 1 the aromatic fragrance generator 10 is disposed on a table and is plugged into an electric outlet 12 to produce an aromatic fragrance 13 into the atmosphere. The aromatic fragrance generator 10 has an external container 14 (or housing) with air intake holes 16 at the bottom and an aromatic fragrance escape port 18 in a cover 19 on top of, and sealing, the external container 14. It is conceptually possible to operate the aromatic fragrance generator without cover 19, however heat efficiency would be lost. An electric cord 21 with switch 22 supply electric current to an electric light bulb 23 (FIG. 2) within the external container 14. The electric light bulb 23 supplies heat to volatilize or aromatize the fragrance base 25 (FIG. 2 and 4). While an electric light bulb is used as the heating element, other heat producing elements may be employed.

Inside of the external container 14 (FIG. 2) there is an electric light bulb 23 supplying heat to a fragrance base 25 held in a heating pan 27. The fragrance base heating pan 27 contains therein a fragrance base 25. For convenience in removing and reinserting the heating pan 27 there is a handle 28 attached to the top of the heating pan 27. The fragrance base heating pan 27 sits on a cylindrical support base 30 having spaced apart feet 32 (FIGS. 2–5) which aid in supplying an updraft of heated air to the heating pan.

Figure 5:
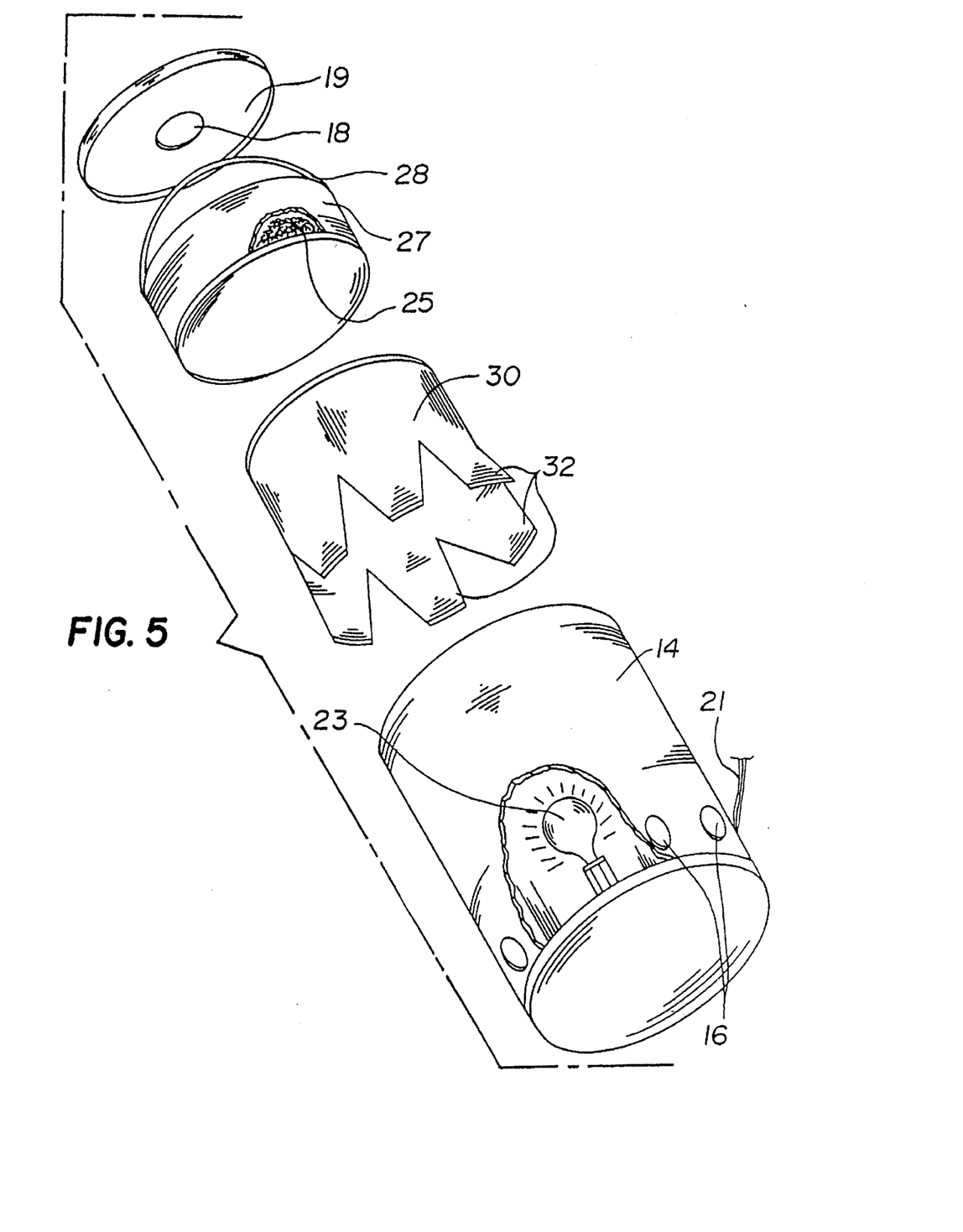
FIG. 5 is an exploded perspective view of the main components of the aromatic fragrance generator (not to scale). Part of the external container has been broken away to show the heating element and part of the fragrance receptacle has been broken away to show fragrance granules.

With reference to FIG. 5 the main components which form the aromatic fragrance generator 10 are the external container 14 with air intake holes 16. An electric light bulb 23 is attached to the inside bottom of the external container. A support base 30 with spaced apart feet 32 fits into the external container 14. The feet 32 of the support base 30 rest on the inside bottom of the external container 14 and surround the electric light bulb 23. The fragrance base heating pan 27 sits on top of the support base 30. Top cover 19 fits snugly on top of the external container 14 which completely houses the electric light bulb 23, the support base 30 and the fragrance base heating pan 27.

Figure 6:
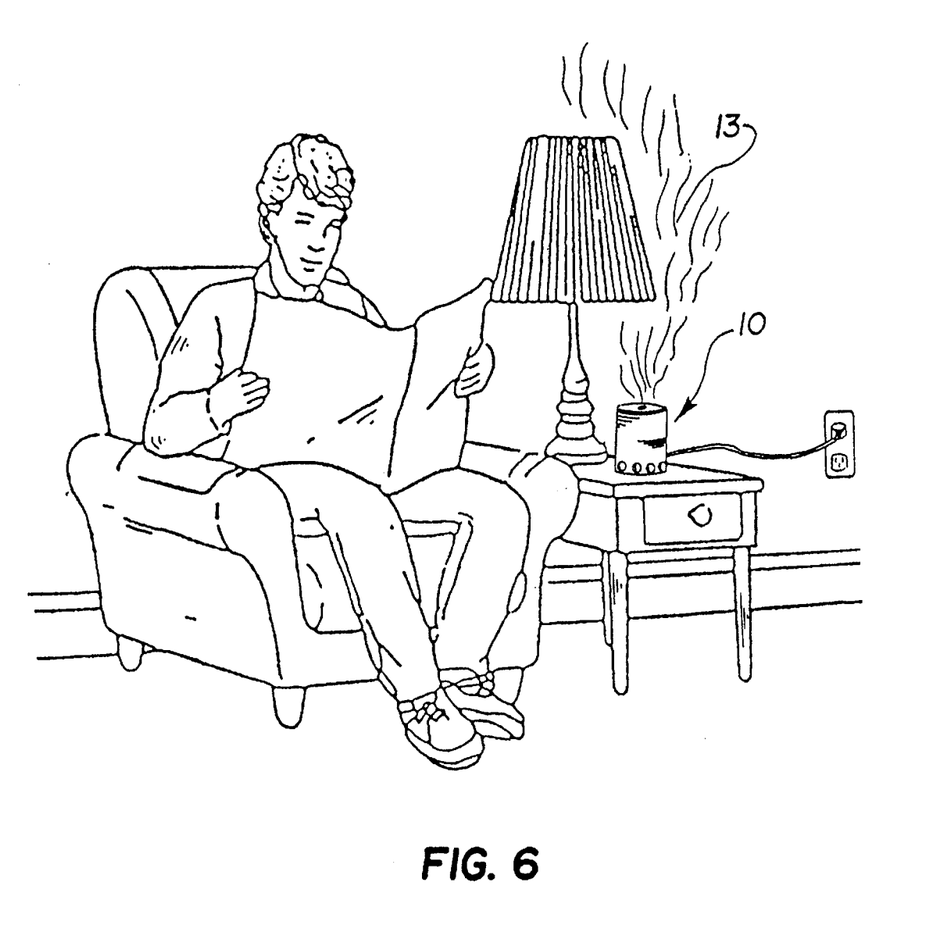
FIG. 6 is a view illustrating the aromatic fragrance generator in use to supply an aromatic fragrance.
Figure 7:
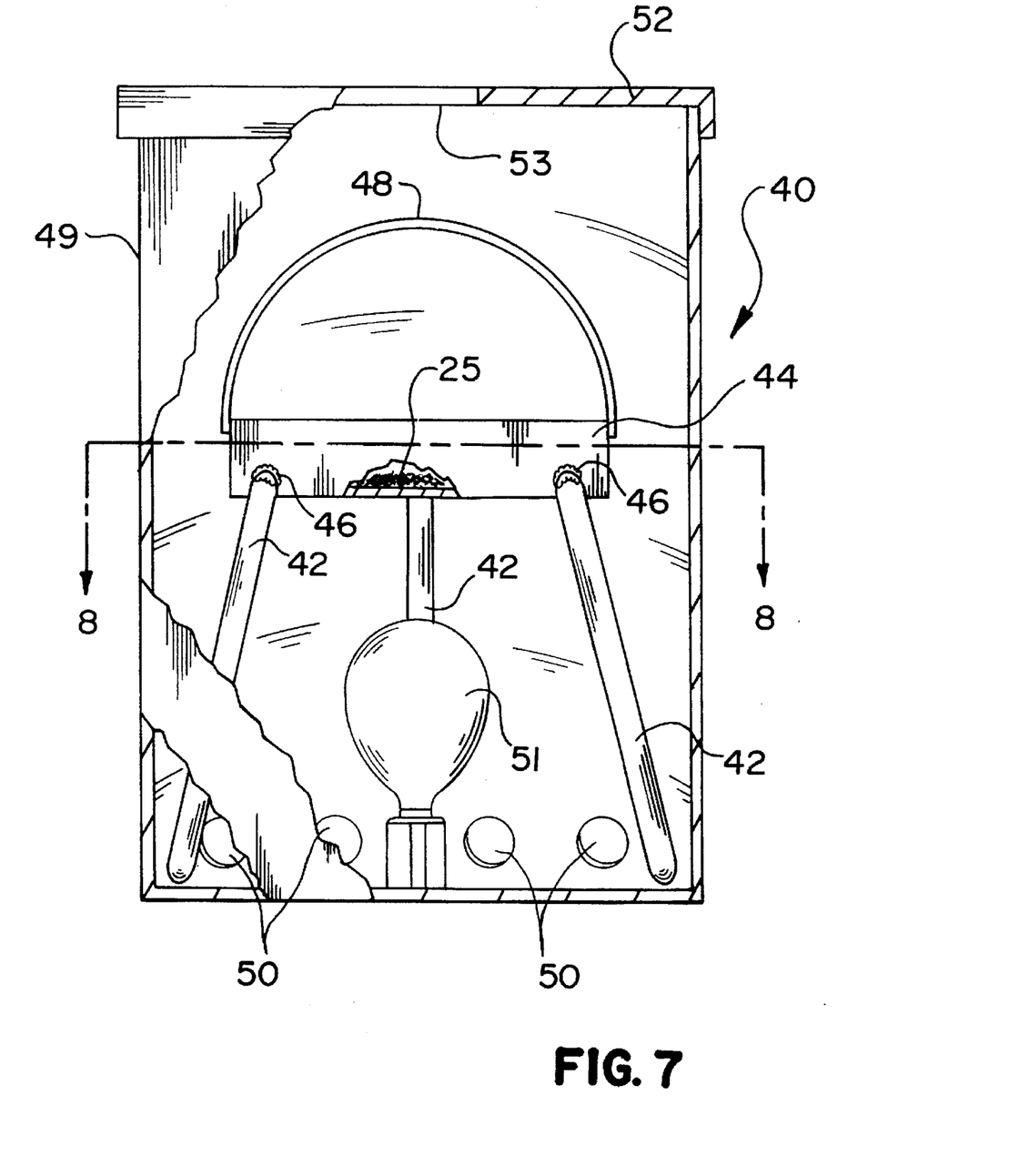
FIG. 7 is an elevational view of an alternative embodiment aromatic fragrance generator. Part of the external container has been broken-away to show internal components; and part of the heating pan has been broken away to show the fragrance base.
Figure 8:
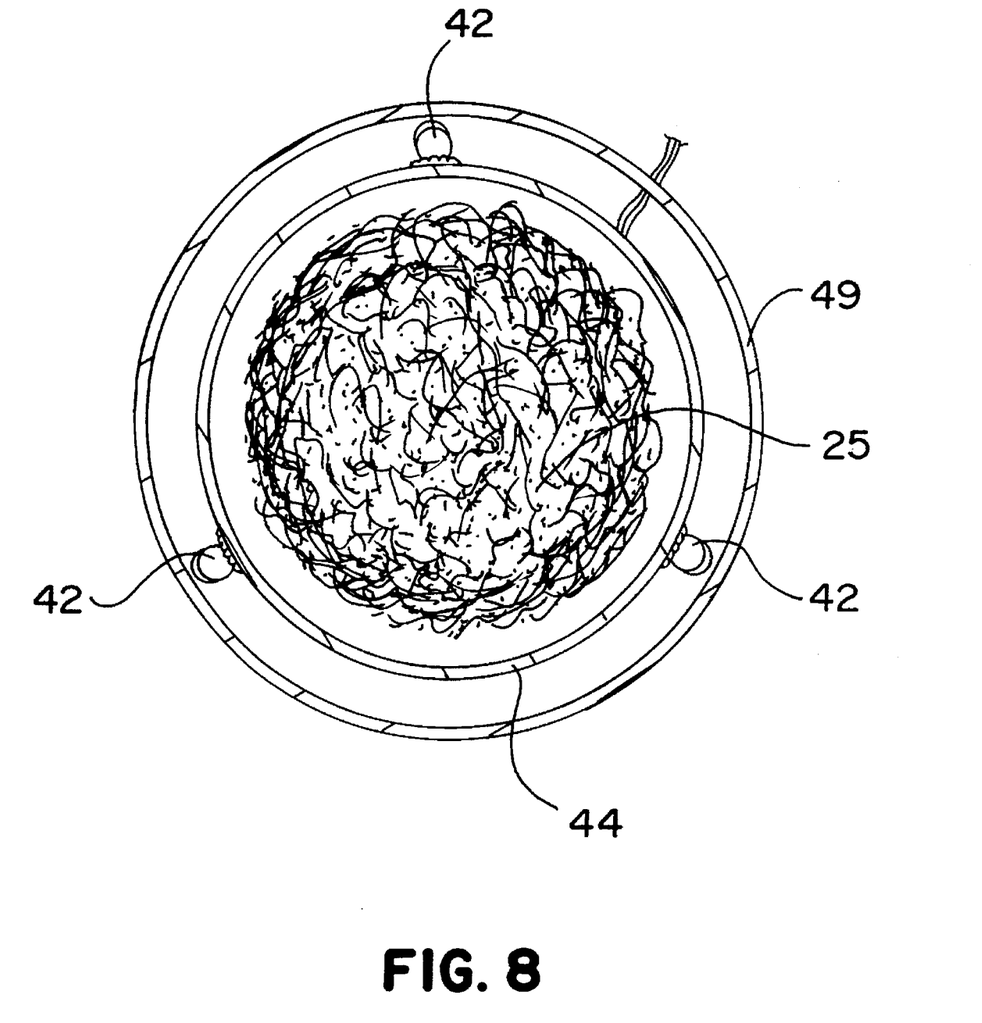
FIG. 8 is a crossection view taken along lines 8—8 of FIG. 7.

With reference to FIG. 7 and 8 an alternative embodiment of the aromatic fragrance generator 40 has three legs 42 projecting from a fragrance base heating pan 44. The legs 42 are attached to the heating pan 44 by spot welding 46, however, other means of attachment such as screws or rivots would be operative. A handle 48 is attached to the heating pan 44 for easy removal from the external container 49. Upon removal the heating pan 44 can be replenished with fragrance base 25. The external container 49 with air-intake holes 50, heating element 51 and top cover 52 with the fragrance escape port 53 are substantially the same as those shown in FIG. 1–6.

Figure 9:
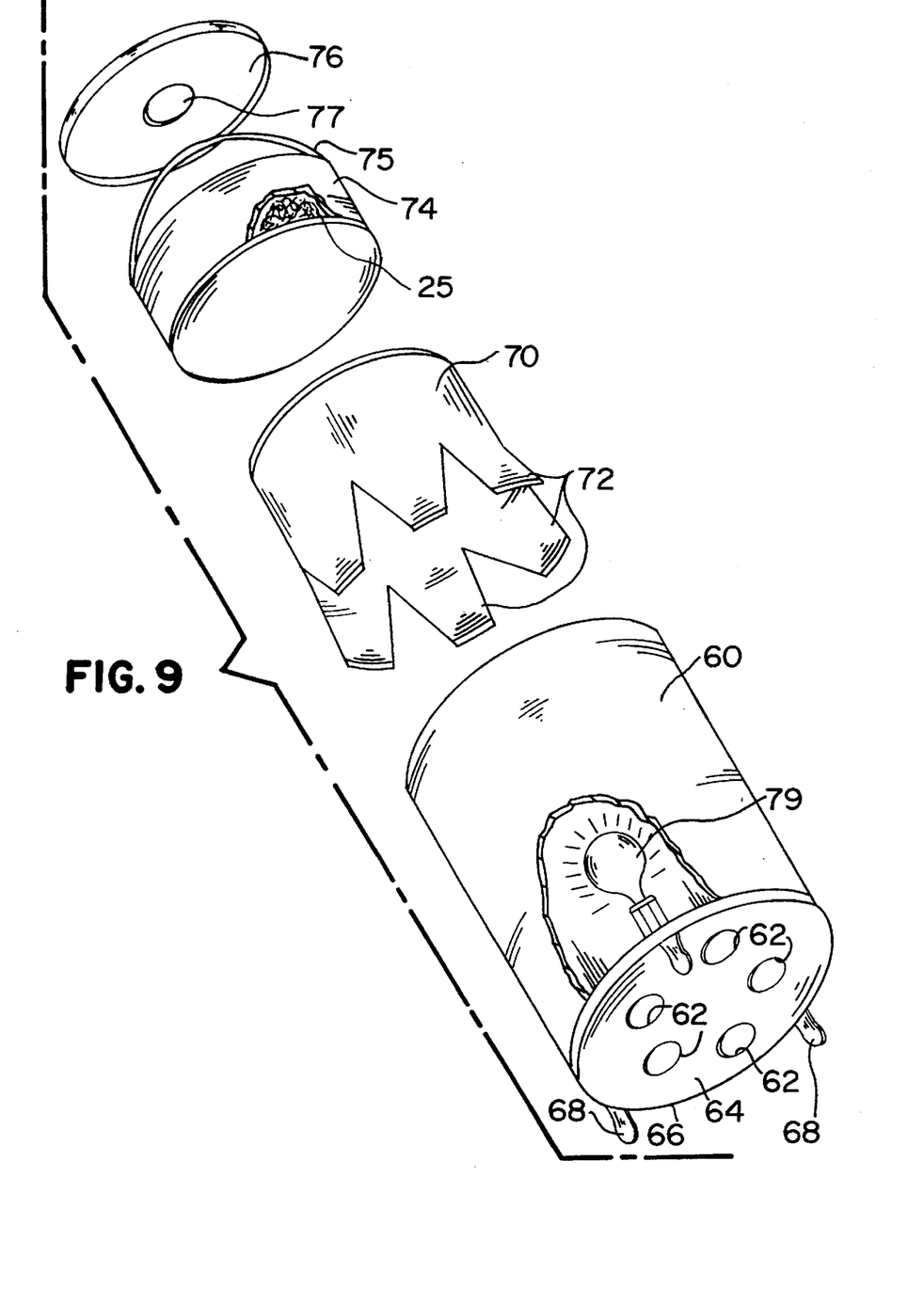
FIG. 9 is an exploded perspective view of the main components of a further alternative embodiment aromatic fragrance generator (not to scale). Part of the external container has been broken away to show the heating element and part of the fragrance receptacle has been broken away to show the fragrance base.

Referring to FIG. 9 a further alternate embodiment of an aromatic fragrance generator has an external container 60 and air-vent holes 62 in the bottom 64 of the container 60. The bottom outer circumference 66 of the container 60 is provided with legs 68 for standing the aromatic fragrance generator on a surface. In use the legs 68 at the bottom outer circumference 66 of the container 60 provide space, allowing air to freely enter the air-vent holes 62 in the bottom 64 of the external container 60. The support base 70 with feet 72, fragrance base heating pan 74 with handle 75, top cover 76 with the fragrance escape port 77 and heating element 79 are substantially the same as in FIGS. 1–6. In the embodiment shown in FIG. 9 there are five air-vent holes and three legs. The number of air-vent holes is not critical; nor is the number of legs. For example, there could be more than three legs. The legs are shown mounted on the bottom of the external container, however they could be attached to the sides of the container.

To operate the aromatic fragrance generator 10 a fragrance base 25 which could be granular coffee, nutmeg, cinnamon or other well known fragrance or fragrant spice (or suitable liquid) is placed in the fragrance base heating pan 27 sitting on the support base 30. The top cover 19 is placed over the external container 14 and the electric light bulb 23 turned-on. The electric bulb 23 heats the heating pan 27 containing fragrance base 25 to produce a pleasant aroma 13 (FIG. 6).

The aromatic fragrance generator (FIGS. 2 and 5) has a unique and efficient construction in that air can be drawn into the external container 14 through the air intake holes 16 and drawn by the heat of the electric light bulb 22 to the fragrance base heating pan to allow the heated fragrance base 25 to give off its aroma through the fragrance escape port 18 of the top cover 19. The spaced apart feet 32 of the support base aid in drawing heated air to the heating pan and the aromatization of the fragrance base. The alternate embodiments of FIGS. 7–9 operate in a fashion similar to that of FIGS. 2–5.

Many advantages accrue from the aromatic fragrance generator of this invention:

The aromatic fragrance generator is able to use ordinary household items (spices, herbs, etc.) as the fragrance base for producing the aroma.

The generator is easy to use and resupply with fresh fragrance producing materials.

The generator is able to use granular or liquid materials as the fragrance base to produce an aroma.

The generator itself is easy to produce out of conventional commercially available material.

When desired a mixture of spices, perfumes and other aromatic components can be used in the aromatic fragrance generator to produce an aromatic bouquet.

Obviously, many modifications may be made without departing from the basic spirit of the present invention. Accordingly, it will be appreciated by those skilled in the art that within the scope of the appended claims, the invention may be practiced other than has been specifically described herein.

I claim:

1. A device for supplying a pleasant aroma to the atmosphere comprising in combination:

an external container having a closed bottom, an open top, and at least one side wall defining the periphery of the container and having air-vent holes at the bottom thereof;

a unitary cover sealing said open top of said external container and having a vent hole therethrough;

an electric heating element disposed within and at the bottom of said external container;

a support surrounding and extending over said heating element and positioned internal to said external container, whereby said support provides insulation for the side walls of the external container;

said support having gaps therein so as to allow air entering the air-vent holes in the external container to pass through the support and up through the vent hole in the cover, creating a draft, said support further providing a base for retaining and concentrating heat on a fragrance base receptacle, said receptacle having a handle attached thereto;

whereby when an aromatic fragrance base is placed in said fragrance base receptacle and the heating element is turned on, the fragrance base will aromatize and produce a pleasant aroma to the ambient atmosphere.

2. The device of claim 1 wherein the external container is cylindrical.

3. The device of claim 1 wherein the heating element is attached to the bottom of said external container.

4. The device of claim 3 wherein the heating element is an electric bulb with electricity supplied by a cord running through said external container.

5. The device of claim 4 further including a switch on the cord.

6. The device of claim 1 wherein the unitary cover has a vent hole in its center.

7. The device of claim 1 wherein the external container, ventilated support and fragrance receptacle are all cylindrical.

8. A fragrance generator for household purposes comprising a housing having an electric socket therein;

a replaceable light bulb in said socket;

means for selectively energizing the bulb thereby providing a source of heat within the housing;

a support surrounding and extending over said light bulb and positioned internal to said housing;

a pan provided with a handle within the housing, supported by said support and disposed in juxtaposition to the bulb, said pan containing an aromatic granular material, which when heated by said light bulb, will cause warm air currents to circulate within the housing and around the pan of heated aromatic granular material and discharge a pleasant aroma out of the housing.

9. The fragrance generator of claim 8 wherein the means for selectively energizing the bulb includes a switch on a cord.

10. A device for supplying a pleasant aroma to the atmosphere comprising in combination an external container having a closed bottom, an open top, and at least one side wall defining the periphery of the container and having air-vent holes at the bottom thereof;

a unitary cover sealing said open top of said external container and having a vent hole therethrough;

an electric heating element disposed within and at the bottom of said external container;

extending over said heating element there is provided a fragrance base receptacle supported by legs which surround the heating element and extend to the bottom of the external container, whereby when an aromatic fragrance base is placed in said fragrance base receptacle and the heating element is turned on, the fragrance base will aromatize and produce a pleasant aroma to the ambient atmosphere.

11. The device of claim 10 wherein the fragrance base receptacle is supported by three legs.

12. A device for supplying a pleasant aroma to the atmosphere comprising in combination:

an external container provided with legs and having a closed bottom, an open top, and at least one side wall defining the periphery of the container and having air-vent holes at the bottom thereof;

a unitary cover sealing said open top of said external container and having a vent hole therethrough;

an electric heating element disposed within and at the bottom of said external container;

a support surrounding and extending over said heating element and positioned internal to said external container, whereby said support provides insulation for the side walls of the external container;

said support having gaps therein so as to allow air entering the air-vent holes in the external container to pass through the support and up through the vent hole in the cover, creating a draft, said support further providing a base for retaining and concentrating heat on a fragrance base receptacle, said receptacle having a handle attached thereto;

whereby when an aromatic fragrance base is placed in said fragrance base receptacle and the heating element is turned on, the fragrance base will aromatize and produce a pleasant aroma to the ambient atmosphere.

13. The device of claim 12 wherein the external container is provided with three legs.

14. An aromatic fragrance generator, comprising a cylindrical can having a closed bottom, an open top, and at least one side wall defining the periphery of the container and having at least one air inlet hole at the bottom thereof;

a removable disc covering the open top of the can, said disc having a central air outlet opening formed therein;

a lamp receptacle located within said can;

a replaceable light bulb disposed within said lamp receptacle;

a support member surrounding and extending over said light bulb and positioned internal to said can;

a lift-out pan supported within the can by said support member and being provided with a bail handle;

whereby when the disc is removed and the bail handle is grasped to lift the pan out of the can, a desired material may be received in the pan, such that when the pan is replaced in the can and the disc fitted over the can, an aromatic fragrance is generated.

* * * * *